United States Patent [19]

Akiyama et al.

[11] Patent Number: 5,341,102
[45] Date of Patent: Aug. 23, 1994

[54] ELECTROMAGNETIC INDUCTION-TYPE CONDUCTIVITY METER WITH IMPROVED CALIBRATION WITH AUXILIARY CIRCUIT

[75] Inventors: Shigeyuki Akiyama; Tatsuhide Tsutsui, both of Miyanohigashi, Japan

[73] Assignee: Horiba, Ltd., Kyoto, Japan

[21] Appl. No.: 893,756

[22] Filed: Jun. 5, 1992

[30] Foreign Application Priority Data

Jun. 8, 1991 [JP] Japan .................. 3-163604

[51] Int. Cl.⁵ ............. G01N 27/06; G01R 27/22; G01R 35/00
[52] U.S. Cl. .................. 324/445; 73/861.11; 324/202; 324/204; 324/239; 324/601
[58] Field of Search ........... 324/439, 442, 445, 601, 324/425, 446, 448, 202, 204, 239, 328, 329; 73/861.08, 861.11

[56] References Cited

U.S. PATENT DOCUMENTS

| | | | |
|---|---|---|---|
| 2,438,197 | 3/1948 | Wheeler | 324/328 X |
| 3,292,077 | 12/1966 | Sloughter | 324/445 |
| 3,855,522 | 12/1974 | Kobayashi | 324/445 |
| 4,084,135 | 4/1978 | Enabnit | 324/239 X |
| 4,761,539 | 8/1988 | Carmean | 324/601 |

FOREIGN PATENT DOCUMENTS

| | | | |
|---|---|---|---|
| 0832435 | 5/1981 | U.S.S.R. | 324/445 |
| 0859895 | 9/1981 | U.S.S.R. | 324/445 |
| 1317349 | 6/1987 | U.S.S.R. | 324/442 |
| 1330584 | 8/1987 | U.S.S.R. | 324/445 |

Primary Examiner—Gerard R. Strecker
Assistant Examiner—Diep Do
Attorney, Agent, or Firm—Price, Gess & Ubell

[57] ABSTRACT

In an improved electromagnetic induction-type conductivity meter utilizing primary and secondary transformer coils about a liquid sample passageway, a resistance circuit having a conductive lead line extending also through the coils and parallel with the sample passageway is provided. The resistance circuit can be selectively opened and closed, and has the capacity to contribute to the measurement voltage detected on the detector coil when the primary coil is excited. The value of this additional resistance voltage can be used for calibration and monitoring the condition of the conductivity meter.

2 Claims, 4 Drawing Sheets

5,341,102

ELECTROMAGNETIC INDUCTION-TYPE CONDUCTIVITY METER WITH IMPROVED CALIBRATION WITH AUXILIARY CIRCUIT

BACKGROUND OF THE INVENTION

1. Field of the Invention

The present invention relates to an electromagnetic induction-type conductivity meter for measuring a conductivity of a sample liquid, such as a solution, utilizing an electromagnetic induction current.

2. Description of Related Art

Conductivity meters have been used to analyze properties of liquid samples. FIG. 4(A) schematically shows a construction of a measuring portion of a conventional electromagnetic induction-type conductivity meter. A housing or case 31 is made of a resin material and is provided with a liquid-flowing passageway 37 consisting of a vertical passageway 33 having an opening 32 at its lower end portion and a horizontal passageway 36 having openings 34, 35 on its (right and left) sides for communicating with the vertical passageway 33. A transformer chamber 40 encloses an exciting transformer 38 and a detecting transformer 39 therein under the condition that they are insulated from each other and formed at one end of the housing 31.

The transformers 38 and 39 are of the same size and their respective iron cores 41, 42 are circular. An exciting coil 43 and a detecting coil 44 are wound around, respectively, iron core 41 and iron core 42. The vertical passageway 33 is arranged so as to pass through the 11 respective centers of the iron cores 41, 42 of both transformers 38, 39.

In an electromagnetic induction-type conductivity meter having the above-described construction, if an alternating voltage having an appointed magnitude and an appointed frequency is applied between the terminals of exciting coil 43 of the exciting transformer 38 under a condition wherein the measuring portion is immersed in a liquid to be measured such as a solution, the liquid to be measured passing through the passageway 33 acts as a one turn coil, whereby an alternating current, $i_c$, resulting from an electromagnetic induction will flow, as shown in FIG. 4(B). Thus, an alternating electromotive force can be induced between the terminals of the detecting coil 44 of the detecting transformer 39. This alternating electromotive force is equal to the alternating voltage applied to the exciting coil 43 in frequency, and its magnitude is proportional to an electrical conductivity of the sample liquid to be measured as it flows through the liquid-flowing passageway 37. Accordingly, the electrical conductivity of the liquid to be measured can be measured by using a calibration liquid, such as an aqueous solution of KCl having an appointed concentration, to preliminarily establish a graph showing a relationship between the alternating electromotive force (mV) and the electrical conductivity (mS/cm) of the calibration liquid.

However, in an electromagnetic induction-type conductivity meter of this type, its detecting sensitivity can be reduced over a period of use, so that it is necessary to periodically check the detecting sensitivity. Accordingly, conventionally, a measurement of electrical conductivity of a sample liquid to be measured must be interrupted to remove the measuring portion from the sample liquid to be measured and to immerse the measuring portion in a calibration liquid, such as an aqueous solution of KCl having an appointed concentration, thereby periodically checking the detecting sensitivity of the instrument.

According to the above-described calibrating method, disadvantages have occurred in that a measurement of the electrical conductivity of a sample liquid to be measured must be interrupted for calibration. If the measuring portion with the calibration liquid adhering to a surface thereof is subsequently immersed in the sample liquid to be measured as it is, the liquid to be measured is contaminated with the calibration liquid.

Thus, the industry is still seeking to simplify and improve the accuracy and use of conductivity meters.

SUMMARY OF THE INVENTION

It is an object of the present invention to provide an electromagnetic induction-type conductivity meter capable of checking a detecting sensitivity without using a calibration liquid.

In order to achieve the above-described object, according to the present invention, in an electromagnetic induction-type conductivity meter having an iron core with an exciting coil wound therearound and an iron core with a detecting coil wound therearound, with both cores being arranged so as to encircle a loop of sample liquid to be measured on the basis of an electromotive force induced in the detecting coil when an alternating signal is applied to the exciting coil, a loop-like stationary resistance circuit having an appointed resistance value is arranged so as to extend through both iron cores, and the stationary resistance circuit is adapted to be opened and closed. A voltage generated by an electrical current, depending upon the electrical conductivity of the liquid to be measured, is output on the side of the detecting coil in the same manner as in the conventional electromagnetic induction-type conductivity meter when the stationary resistance circuit is opened. However, when the stationary resistance circuit is closed, a voltage obtained by adding a voltage generated by an electrical current, depending upon a resistance of the stationary resistance circuit to the voltage output on the side of the detecting coil, is also output on the side of the detecting coil. The signals of the above-described respective voltages are suitably operated upon, checking for the sensitivity of the detecting system, calibrating the sensitivity, and judging the existence of any abnormal situation.

An electromagnetic induction-type conductivity meter system includes a housing with a sample passageway. A primary coil and a secondary coil extend about the sample passageway. A generator can apply an alternating current to the primary coil. A resistance circuit, including a connector wire, interconnects the primary and secondary coils, and a switch can open and close the resistance circuit. A computer system with appropriate interface components can store in a memory a digital value of a first voltage generated by the resistance circuit in the secondary coil when closed and subject to a predetermined alternating current, to establish a reference voltage level. A calibration factor can be derived by generating a second subsequent voltage in the secondary coil with a closed resistance circuit and providing the calibration factor from the first and second voltage. A voltage of a sample liquid generated in the secondary coil with the resistance circuit in an open condition can then be modified with the calibration factor to provide an output signal.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved calibration feature to a conductivity meter.

The preferred embodiments of the present invention will now be described with reference to the drawings.

Figure 1:
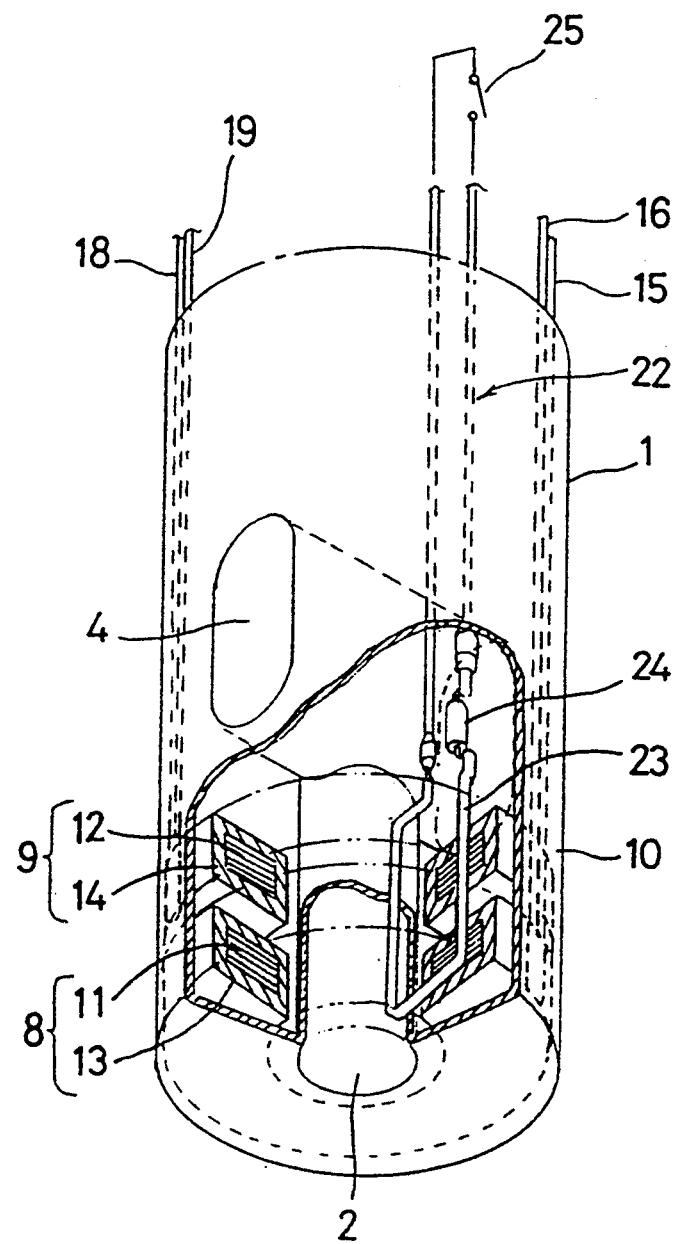
FIG. 1 is a partially cross-sectional perspective view showing the parts of an electromagnetic induction-type conductivity meter according to the present invention.
Figure 2:
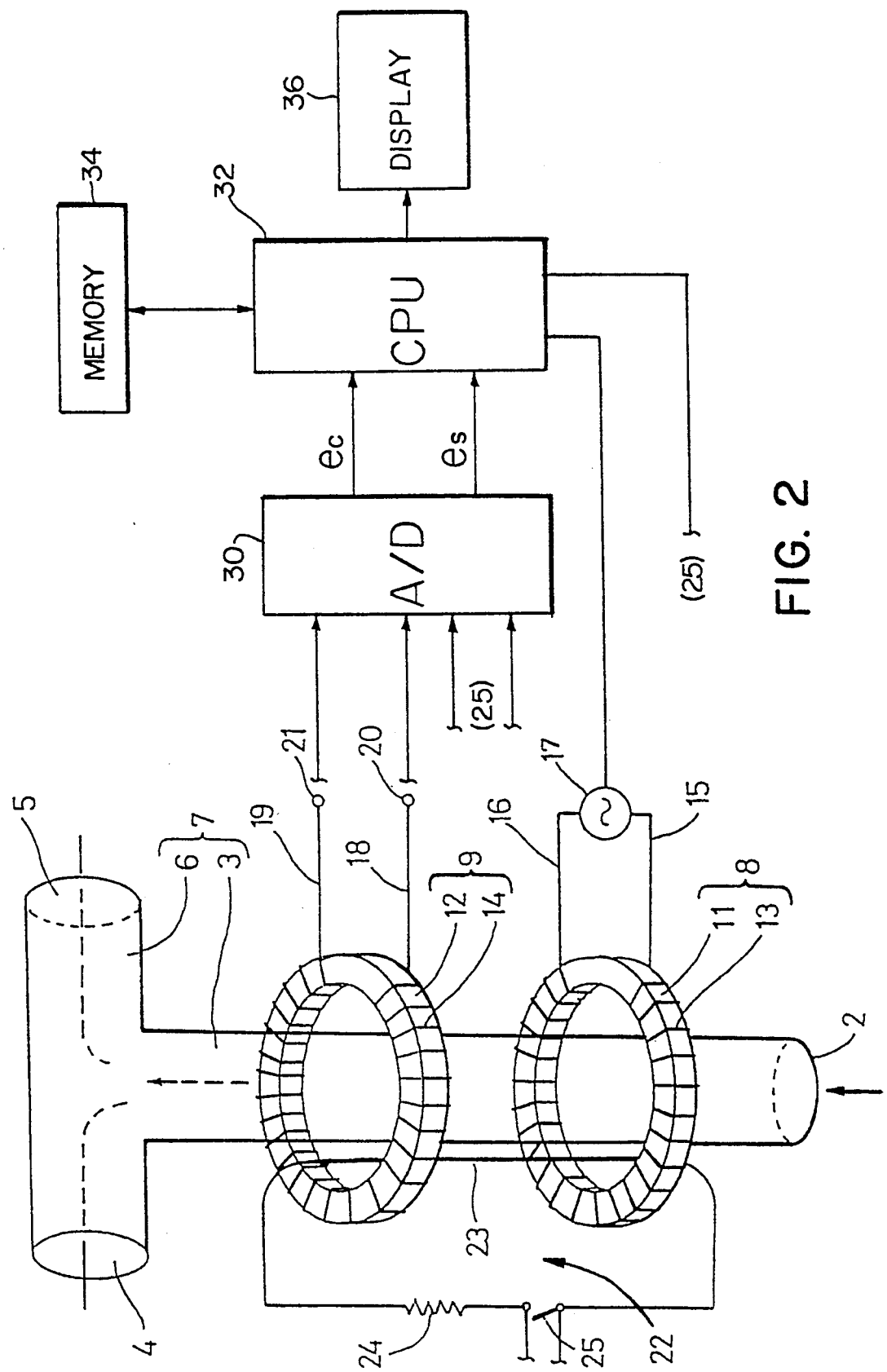
FIG. 2 is a schematic diagram showing an electrical construction in the electromagnetic induction-type conductivity meter.

Referring to FIGS. 1 and 2, showing the essential components of the electromagnetic induction-type conductivity meter of the present invention, reference numeral 1 designates a case made of plastic resins which have superior insulation and corrosion resistance characteristics, such as PFA (per fluoro alkyl vinyl ether), PVC (poly vinyl chloride), and PVdF (poly vinyliden fluoride). The case or housing 1 is provided with a liquid-flowing passageway 7 consisting of a longitudinal vertical passageway 3 having an opening 2 at its lower end portion and a horizontal passageway 6 having openings 4 and 5 on its respective right and left sides and communicated traversely with the vertical passageway 3. A transformer chamber 10 houses an exciting or primary transformer 8 and a detecting or secondary transformer 9 therein under a condition that they are electrically insulated from each other and are formed at a pointed end of the housing 1.

The transformers 8 and 9 have the same size circular iron cores 11 and 12. An exciting coil 13 and a detecting coil 14 are wound around the iron core 11 and the iron core 12, respectively. The vertical passageway 3 is arranged so as to pass through the respective centers of the iron cores 11 and 12 of both transformers 8 and 9. Reference numerals 15 and 16 designate lead wires connected with the exciting transformer 8 and connected with an alternating power source 17 at end portions thereof. In addition, reference numerals 18 and 19 designate a lead wire extending from the detecting transformer 9 and provided with an output terminals 20 and 21 at an end portion thereof, respectively, and thus connected with an operation-controlling portion (not shown). The operation-controlling portion can sense the induced current as a signal representative of a condition of the sample liquid. The value of the signal can be used to both monitor the operability of the meter on a display 36 and also to calibrate the instrument based on the assumption of a linear relationship of a ratio of the measured signal to a predetermined output.

Reference numeral 22 designates a loop-like stationary resistance circuit extending through the respective iron cores 11 and 12 in a parallel manner to the passageway 3. The stationary resistance circuit 22 includes a lead wire 23, a resistance or resistor 24 having an appointed resistance value, and an on-off switch 25 so as to open or close the circuit 22. As can be seen, the lead wire 23 need not be in the fluidic passageway 3.

In one embodiment, the operation-controlling portion can constitute an appropriate conversion of the voltage signal, $e_c$, across the output terminals 20 and 21 by an A/D converter 30, and a storing of that value through an I/O interface circuit (not shown) into an operating CPU 32 with appropriate memory 34. The CPU can also control the alternating power source 17. The voltage signal, $e_s$, across the switch 25 is also converted into a digital value and stored for subsequent processing.

Figure 3:
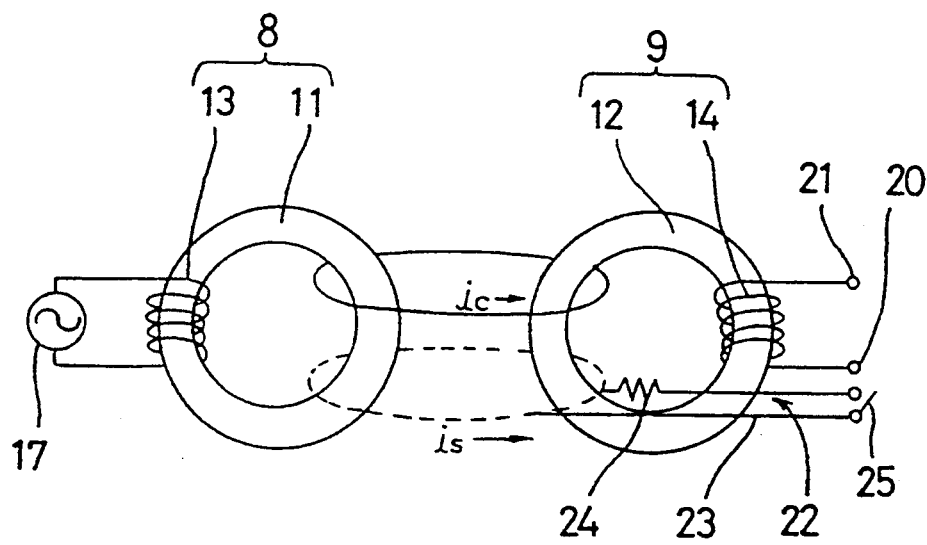
FIG. 3 is a schematic diagram for describing an operation according to the present invention.
Figure 4A:
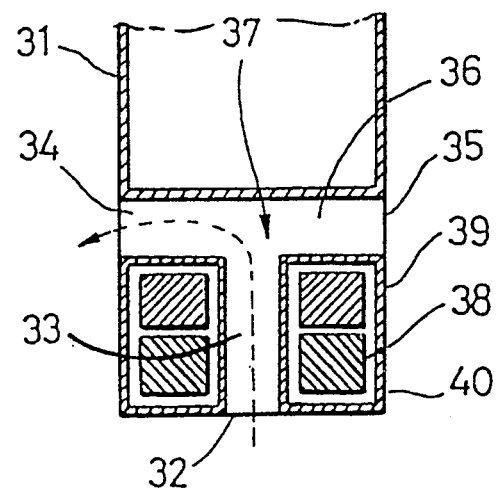
FIG. 4(A) is a longitudinal cross-sectional view showing parts of the conventional electromagnetic induction-type conductivity meter.
Figure 4B:
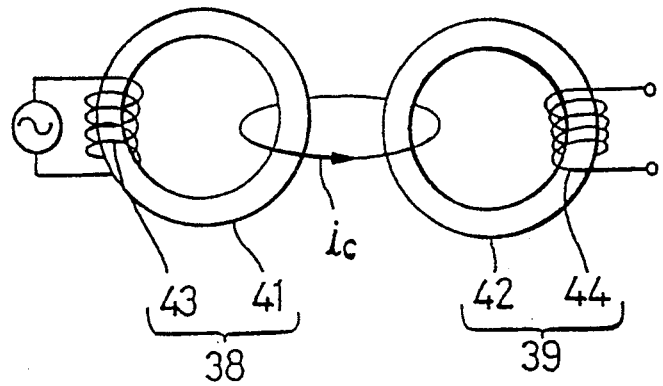
FIG. 4(B) is a diagram for describing an operation of the conventional electromagnetic induction-type conductivity meter.

Next, an operation of an electromagnetic induction-type conductivity meter having the above-described construction will be described with reference to FIG. 3. If the on-off switch 25 is open or closed under a condition that a sample liquid, to be measured, flows in the direction shown by an arrow in FIG. 2, a voltage is output between the output terminals 20 and 21 of the detecting transformer 9.

When the on-off switch 25 is opened, the voltage $e_c$ generated by an electrical current $i_c$, depending upon a conductivity of the liquid to be measured, is output between the output terminals 20 and 21. This is quite similar to that in the conventional electromagnetic induction-type conductivity meter. However, when the on-off switch 25 is closed, a different voltage value is obtained by adding a voltage $e_s$ generated by an electrical current $i_s$, depending upon the value of the resistance 24 to the voltage $e_c$, is output between the output terminals 20 and 21. These output voltages are expressed as follows:

$$e_{OFF} = e_c$$

$$e_{ON} = e_c + e_s$$

A differential voltage ($e_{ON} - e_{OFF} = e_s$) between the voltage $e_{ON}$ and the voltage $e_{OFF}$ has a constant value as long as the exciting coil 13 and the detecting coil 14 remain in a normal operating condition. However, if the respective parts deteriorate in a manner so as to change the voltage $e_{ON}$ and the voltage $e_{OFF}$, the voltage $e_s$ is also changed. In the case where values of the above-described respective voltages are changed, a check of the detecting system sensitivity, a calibration of the measured value in sensitivity, and a judgment of the existence of an abnormal situation and the like can be achieved by suitably monitoring these values in an operating-controlling portion and comparing the measured value with a predetermined value in a comparator circuit (not shown). As mentioned above, a software program can alternatively perform these operations in an operating CPU 32 and display the results on display 36.

Provided that the voltage $e_{OFF}$ between the output terminals 20 and 21 during the time when the on-off switch 25 is opened is $e_c$, and the voltage $e_{ON}$ between the output terminals 20 and 21 during the time when the on-off switch 25 is closed is $e_c'+e_s'$, the difference between both voltages at that time becomes $e_s'$. Thus, voltage $e_s$ can be compared with the voltage $e_s'$ to obtain $e_s'/e_s$. A value of this $e_s'/e_s$ is compared with an appointed value to be able to determine the sensitivity of the detecting system. If the ratio $e_s'/e_s$ is within a permissible range, then $e_c' \times d_s'/e_s$ can be used as an electrical conductivity coefficient for calibrating the sensitivity.

In addition, when the voltage $e_s'$ is nearly equal to zero, it is judged that at least one of the exciting coil 13 and the detecting coil 14 is disconnected. Moreover, when the voltage $e_s'$ is larger than the standard value, it can be judged that the exciting coil 13 is short-circuited.

In addition, if the resistance value of the stationary resistance circuit 22 is constant, the resistance 24 is not always required. Also, although the resistance 24 is provided within the case 1 in the above-described preferred embodiment, it may alternatively be provided in the operating-controlling portion. In the case of a sample having a relatively high conductivity (10 to 1,000 mS/cm), the full scale of the conductivity meter is 1,000 mS/cm, and a fixed resistance of 5Ω corresponds to 1,000 mS/cm.

According to the present invention, a check of the detecting system sensitivity, a calibration of the measured value in sensitivity, and a judgment of the existence of any disconnection and short-circuit in the coils and the like can be achieved while the electrical conductivity of the sample liquid is measured. Accordingly, the sensitivity of the instrument can be checked without using a calibration liquid and interrupting the measurement of electrical conductivity. As a result, the measuring efficiency of electrical conductivity can be improved and calibration liquid will not contaminate the sample liquid. In addition, a superior effect is obtained in that the calibration of the measured value in sensitivity and the judgment of the existence of any disconnection or short-circuit in the coils and the like can be conducted at the same time as a check of the detecting system sensitivity.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An electromagnetic induction-type conductivity meter comprising:

a housing with a sample passageway;

a primary coil extending about the sample passageway;

a secondary coil extending about the sample passageway and sufficiently close to be linked by electromagnetic flux with the primary coil by the sample passageway;

means, connected to the primary coil, for providing an alternating current to the primary coil;

a circuit means extending between the primary and secondary coils for providing a voltage signal that can be sensed by the primary and secondary coils, including means for activating and deactivating the circuit means;

means for storing a value of a first voltage induced by the circuit means in the secondary coil when the circuit means is activated and subject to a predetermined alternating current;

means for providing a calibration factor including generating a second subsequent voltage in the secondary coil with an activated circuit means and providing the calibration factor from the first and second voltages;

means for measuring a voltage of a sample liquid from the secondary coil with the circuit means in a deactivated condition, and means for modifying the sample liquid voltage with the calibration factor to provide an output signal representative of the sample liquid.

2. The invention of claim 1 wherein the circuit means is mounted adjacent the sample passageway.

* * * * *